US006703396B1

(12) United States Patent
Liotta et al.

(10) Patent No.: US 6,703,396 B1
(45) Date of Patent: Mar. 9, 2004

(54) METHOD OF RESOLUTION AND ANTIVIRAL ACTIVITY OF 1,3-OXATHIOLANE NUCLESOSIDE ENANTIOMERS

(75) Inventors: Dennis C. Liotta, Stone Mountain, GA (US); Raymond F. Schinazi, Decatur, GA (US); Woo-Baeg Choi, North Brunswick, NJ (US)

(73) Assignee: Emory University, Atlanta, GA (US)

( * ) Notice: Subject to any disclaimer, the term of this patent is extended or adjusted under 35 U.S.C. 154(b) by 641 days.

(21) Appl. No.: 08/402,730

(22) Filed: Mar. 13, 1995

Related U.S. Application Data

(63) Continuation of application No. 08/092,248, filed on Jul. 15, 1993, now abandoned, which is a continuation of application No. 07/736,089, filed on Jul. 26, 1991, now abandoned, which is a continuation-in-part of application No. 07/659,760, filed on Feb. 22, 1991, now Pat. No. 5,210,085, which is a continuation-in-part of application No. 07/473,318, filed on Feb. 1, 1990, now Pat. No. 5,204,466.

(30) Foreign Application Priority Data

| Mar. 6, 1991 | (GB) | 9104741 |
|---|---|---|
| May 2, 1991 | (GB) | 9109505 |

(51) Int. Cl.[7] .................................................. A61K 31/505
(52) U.S. Cl. .................. 514/274; 514/86; 544/243; 544/317
(58) Field of Search .................. 544/243, 317; 514/274, 86

(56) References Cited

U.S. PATENT DOCUMENTS

| 4,000,137 A | 12/1976 | Dvonoch et al. | 544/313 |
|---|---|---|---|
| 4,336,381 A | 6/1982 | Nagata et al. | 544/313 |
| 4,861,759 A | 8/1989 | Mitsuya et al. | 514/46 |
| 4,879,277 A | 11/1989 | Mitsuya et al. | 514/49 |
| 4,900,828 A | 2/1990 | Belica et al. | 544/317 |
| 4,916,122 A | 4/1990 | Chu et al. | 514/50 |
| 4,963,533 A | 10/1990 | de Clerq et al. | 514/49 |
| 5,041,449 A | 8/1991 | Belleau et al. | 514/274 |
| 5,047,407 A | 9/1991 | Belleau et al. | 544/317 |
| 5,059,690 A | 10/1991 | Zahler et al. | 544/276 |
| 5,071,983 A | 12/1991 | Koszalka et al. | 544/317 |
| 5,179,104 A | 1/1993 | Chu et al. | 544/310 |
| 5,185,437 A | 2/1993 | Koszalka et al. | 544/317 |
| 5,204,466 A * | 4/1993 | Liotta et al. | 544/317 |
| 5,210,085 A * | 5/1993 | Liotta et al. | 544/317 |
| 5,234,913 A | 8/1993 | Furman, Jr. et al. | 514/49 |
| 5,248,776 A | 9/1993 | Chu et al. | 544/310 |
| 5,270,315 A | 12/1993 | Belleau et al. | 544/265 |
| 5,538,975 A | 7/1996 | Dionne | |
| 5,618,820 A | 4/1997 | Dionne | |
| 5,814,639 A | 9/1998 | Liotta et al. | |

FOREIGN PATENT DOCUMENTS

| EP | 0 217 580 | 4/1987 |
|---|---|---|
| EP | 0337713 | 4/1989 |
| EP | 0 361 831 | 4/1990 |
| EP | 0375329 | 6/1990 |
| EP | 0433898 | 6/1991 |
| EP | 0515157 | 5/1992 |
| EP | 0494119 | 7/1992 |
| EP | 494119 | 7/1992 |
| EP | 0515144 | 11/1992 |
| EP | 0515156 | 11/1992 |
| EP | 0526253 | 2/1993 |
| WO | WO 88/07532 | 10/1988 |
| WO | WO 90/12023 | 10/1990 |
| WO | WO 91/11186 | 8/1991 |
| WO | WO 91/17159 | 11/1991 |
| WO | WO 92/08717 | 5/1992 |
| WO | WO 92/10496 | 6/1992 |
| WO | WO 92/10497 | 6/1992 |
| WO | WO 92/14743 | 9/1992 |
| WO | WO 92/15308 | 9/1992 |
| WO | WO 92/18517 | 10/1992 |
| WO | WO 94/04154 | 3/1994 |

OTHER PUBLICATIONS

Daniels, T.C. et al. *Textbook of Organic Medicinal and Pharmaceutical Chemistry*, ed. by Wilson, C.O. et al. (Lippincott Co., Philadelphia), pp. 31–36 (1977).*

Carter, S.O. et al. *Antimicrob. Agents Chemotherapy*, vol. 34, pp. 1297–1300 (1990).*

March, J. *Advanced Organic Chemistry* (Wiley and Sons, New York), pp. 82–107 (1985).*

Belleau, B., et al., "Design and Activity of a Novel Class of Nucleoside Analogs Effective Against HIV–1," *International Conference on AIDS*, Montreal, Quebec, Canada Jun. 4–9, 1989.

Krenitsky, T.A., et al., "3'–Amino–2',3'–Dideoxyribonucleosides of Some Pyrimidines: Synthesis and Biological Activities," *J. Med. Chem*, Vo. 26 (1993).

Sterzycki, R.Z., et al., "Synthesis and anti–HIV activity of several 2'–fluoro–containing pyrimidine nucleosides," *J. Med. Chem.* 33:2150–2157 (1990).

Storer, B., et al., "The Resolution and Absolute Stereochemistry of the Enantiomeris of cis–1–[2–(Hydromethyl)–1,3–Oxathiolan–5–yl)cytosine (BCH189): Equipotent Anti–HIV Agents," *Nucleosides & Nucleotides*, 12(2) 225–236 (1993).

(List continued on next page.)

Primary Examiner—James O. Wilson
(74) Attorney, Agent, or Firm—Sherry M. Klowles, Esq.; King & Spalding

(57) ABSTRACT

A process for the resolution of a racemic mixture of nucleoside enantiomers that includes the step of exposing the racemic mixture to an enzyme that preferentially catalyzes a reaction in one of the enantiomers. The nucleoside enantiomer (−)-2-hydroxymethyl-5-(5-flurocytosin-1-yl)-1,3-oxathiolane is an effective antiviral agent against HIV, HBV, and other viruses replicating in a similar manner.

28 Claims, 5 Drawing Sheets

OTHER PUBLICATIONS

Van Roey, P., "Solid State Conformation of Anti–Human Immunosudeficiency Virus Type–1 Agents: Crystal Structures of Three 3'–Azido–3'–deoxythymidine Analogues," *J. Am. Chem. Soc.* (1988) 110, pp. 2277–2782.

Wilson, L.J., et al., "The Synthesis and Anti–HIV Activity of Pyrimidine Dioxolanyl Nucleosides," *Bioorganic & Medicinal Chemistry Letters,* 13(2), pp. 169–174 (1993).

Balzarini, J., et al., "Potent and Selective Anti–HTI V–III/I AV Activity of 2',3'–Dideoxycytidinene, the 2'–3'–Unsaturated Derivative of 2',3'–Dideoxycytidine," *Biochemical and Biophysical Reserach Communications,* vol. 140, No. 2, pp. 735–742 (1986).

Carter et al., "Activties of (–)–Carbovir and 3'–Azido–3'–Deoxythymidine Against Human Immunodeficiency Virus In Vitro," *Antimicrobial Agents and Chemotherapy,* vol. 34, No. 6, pp. 1297–1300 (1990).

Chang, Chien–Neng, et al., "Deoxycytidine Deaminase–resistant Stereoisomer Is the Active Form of (±)–2', 3'–Dideoxy–3'–thiacytidine in the Inhibition of Hepatitis B Virus Replication," *The Journal of Biological Chemistry,* vol. 357, No. 20, pp. 13938–13942 (1992).

Chu et al., "Structure–Activity Relationships of Pyrimidine Nucleosides as Antiviral Agents for Human Immunodeficiency Virus Type 1 in Peripheral Blood Mononuclear Cells," *J. Med. Chem.* vol. 32, p. 612 (1989).

Chu, et al., "Comparative Activity of 2',3'–Saturated and Unsaturated Pyrimidine and Purine Nucleosides Against Human Immunodeficiency Virus Type 1 in Peripheral Blood Mononuclear Cells," *Biochem. Pharm.,* vol. 37, No. 19, pp. 3543–3548 (1988).

Chu, C.K., et al., "An Efficient Total Synthesis of 3'–Azido–3'–Deoxythiymidine (AZT) and 3'–Azido–2', 3'–Dideoxyuridine (AZDDU, CS–87) from D–Mannitol," *Tetrahedron Lett.* 1988, 5349.

Cretton, E., et al., "Catabolism of 3'–Azido–3'–Deoxythymidine in Hepatocytes and Liver Microsomes, with Evidence of Formation of 3'–Amino–3'–Deoxythymidine, a Highly Toxic Catabolite for Human Boane Marrow Cells," *Molecular Pharmacology,* vol. 39, pp. 258–266 (1991).

Cretton, E., et al., "Pharmokinetics of 3'–Azido–3'–Dexoythymidine and its Catabolites and Interactions with Probenecid in Rhesus Monkeys," *Antimicrobial Agents and Chemotheraphy,* pp. 801–807 (1991).

Furman, et al., "The Anti–Hepatitis B Virus Activities, Cytotoxicities, and Anabolic Profiles of the (–) and (+) Enantiomers of cis–5–Fluoro–1–[2–(Hydromethyl)–1, 3–Oxthiolan–5–yl]Cytosine," *Antimicrobial Agents and Chemotherapy,* vol. 36, No. 12, pp. 2686–2692 (1992).

Jeong, L., et al., "Asymmetric Synthesis and Biological Evaluation of β–L–(2R,5S)– and α–L–(2R–5R)–1,3–Oxathiolane–Pyrimidine and –Purine Nucleosides and Potential Anti–HIV Agents," *J. Med. Chem.,* vol. 36 (1993).

Lin, et al., "Potent and Selective In Vitro Activity of 3'–Deoxythmindin–2–Ene–(3'–Deoxy–2+,3'–Didehydrothymidine) Against Human Immunodeficiency Virus," *Biochem. Pharm.,* vol. 36, No. 17, p. 2716 (1987).

Mitsuya, H., et al., "Rapid in Vitro Systems for Assessing Activity of Agents Against HTLV–III/LAV," *AIDS: Modern Concepts and Therapeutic Challenges,* S. Broder, Ed. (Marcel–Dekker, New York, 1987), pp. 303.

Mitsuya, J., et al., 3'–Azido–3'–Deoxythymidine (BW A 509U): An Antiviral Agent that Inhibits the Infectivity and Cytopathic Effect of Human T–Lymphotropic Virus Type III/Lymphadenopathy–Associated Virus In Vitro, *Proc. Natl. Acad. Sci., USA,* vol. 82, pp. 7097–7100 (1985).

Mitsuya, H., et al., "Molecular Targets for AIDS Therapy," *Science,* vol. 249, pp. 1533–1544. (1990).

Norbeck, D., et al., "A New 2',3'–Dideoxynucleoside Prototype with In Vitro Activity Against HIV," *Tetrahedron Lett.* 1989, 6263.

Okabe, M., et al., "Synthesis of the Dideoxynucleosides ddC and CNT from Glutamic Acid, Ribonolactone, and Pyrimidine Bases," *J. Org. Chem.* 1989.

Richman, D. D., et al., "The Toxicity of Azidothymidine (AZT) in the Treatment of Patients with AIDS and AIDS–Related Complex," *N. Eng. J. Med.* 1987, 317:192.

Satsumabayashi, S. et al., "The Synthesis of 1,3–Oxathiolan–5–one Derivatives," *Bull, Chem. Soc. Japan,* 1972, 45,913.

Schinazi, R.F., et al., "Activities of the Four Optical Isomers of 2'–3'–Dideoxy–3'–Thiacytidine (BCH–189) against Human Immunodeficiency Virus Type 1 in Human Lymphocytes," *Antimicrobial Agents and Chemotherapy* 36(3) 672–676 (1992).

Schinazi, R.F., et al., "Insights into HIV Chemotherapy," *AIDS Research and Human Retroviruses* 8(6) (1992) 963–990.

Schinazi, R.F., et al., "Pharmacokinetics and Metabolism of Racemic 2'–3'–Dideoxy–5–Fluoro–3'–Thiacytidine in Rhesus Monkeys," *Antimicrobial Agents and Chemotherapy* 36(11) 2432–2438. (1992).

Schinazi, R.F., et al., "Selective Inhibition of Human Immunodeficiency Viruses by Racemates and Enantiomers of cis–5–Fluoro–1–[2–(Hydroxymethyl)–1, 3–Oxathiolan–5–yl]Cytosine," *Antimicrobial Agents and Chemotherapy* 36(11) 2423–2431. (1992).

Schinazi, R.F., et al., "Substrate Specificity of *Escherichia coli* Thymidine Phosphorylase for Pyrimidine Nucleoside with an Anti–Human Immunodeficiency Virus Activity," *Biochemical Pharmacology* 44(2) (1992) 199–204.

Vorbrüggen et al, "Nucleoside Synthesis with Trimethylsilyl Triflate and Perchlorate as Catalysts," *Chem. Ber.* 1981, 114:1234–1255.

Wilson, L.J., et al., "A General Method for Controlling Glycosylation Stereochemistry in the Synthesis of 2'–Deoxyribose Nucleosides," *Tetrahedron Lett.* 1990, 1815.

Zhu, Zhou, et al., "Cellular Metabolism of 3'–Azido–2', 3'–Dideoxyuridine with Formation 5'–O–Diphophoshexase Derivative by Previously Unrecognized Metabolic Pathways of 2'–Deoxyuridine Analogs," *Molecular Pharmacology,* vol. 38, pp. 929–938 (1990).

Soudeyns, et al., "Anti–Human Immunodeficiency Virus Type 1 Activity and In Vitro Toxicity of 2'–Deoxy–3'–Thiacytidine (BCH–189), a Novel Heterocyclic Nucleoside Analog," *Antimicrobial Agents And Chemotherapy,* pp. 1386–1390 (1991).

Shin–Lian, et al., *Natl. Acad. Sci.* 88, 8495 (1991).

ASAI, *J. Chem. Pharm. Bull,* 1967, 1863–1870, 15(12).

Armstrong, Chiral Stationary Phase 1984.

Armstrong, Chromatographic Chiral Separation, 1986, vol. 40.

Armstrong, Analytical Chemistry, 1987, 84–91, 59(2).

Allenmark, Chromographic Enantioseparation: Method and Applications, 1988.

Balzarini, J. Med. Chem, 1985, 1385–1386, 28.
Balzarini, J. Med. Chem, 1989, 1861–1865, 32.
R. Baum and R. Dagoni, Chemical Engineering News, Jun. 26, 1989, p. 11.
Beach, J. Org. Chem., 1992, 2217–2219, 57.
Belleau, Aids Abstract, 1989, 515.
Belleau, Aids Abstract, 1989, 552.
Boehm, Anal. Chem., 1988, 522–528, 60.
Bzowska, Biochemical Pharmacology, 1991, 1709–1803, 41(12).
Carruthers, Some Modern Methods Of Organic Synthesis, 1986.
Coates, Antimibrobial Agents and Chemtherapy, Jan. 1992, 202–205.
Collet, Enantiomers, Racemates, and Resolutions, 1981.
Dappen, Journal of Chromatography, 1986, 1–20, 373.
Davies, Biotransformations in Preparative Organic Chemistry, 1989.
Eliel, Ernest, *Stereochemistry of Carbon Compounds,* John Wiley & Sons, 1962, p. 328.
Greene, *Protective Groups In Organic Synthesis,* John Wiley & Sons, 1981, pps. 10–72.
Forsman, J. of Chromatography, 1984, 217–221, 303.
Han, J. of Chromatography, 1988, 376–381, 441.
Hesse, Chromatographia, 1973, 277–280, 6(6).
Hinze, Anal. Chem. 1985, 237–232, 57.
Hooper, Clinical Pharmacology and Therapeutics, 1990, 633–640, 48(6).
Holy, Chem. Commun., 1971, 3282–3299, 36.
Humber, Tetrahedron Letters, 1992, 4625–4628, 33(32).
Ikeda, Chemistry Letters, 1989, 1089–1090.
Johnson, J. of Chromatography, 1984, 449–452, 291.
D24 Jones, Illustrative Examples of Enzymes in Organic Synthesis, 1986.
D25 Jones, Enzymes in Organic Synthesis, Tetrahedron, 42:13 1986.
D13 Kim, J. Med. Chem. 30:1987.
Kim, J. Med. Chem., 1987, 862–866, 30.
Lin, J. Med. Chem., 1988, 336–340, 31.
Lipkpwitz, Anal. Chem., 1986, 1611–1617, 58.
Lim, Drug Metabolism and Disposition, 1989, 212–217, 17(2).
Lindner, J. of Chromatography, 1980, 308–310, 193.
D14 Lin, J. Med. Chem. 32:1989.
D19 Mackie and Smith, Guidebook to Organic Synthesis, 1982.
76 Lin Synthesis and Antivity 1976.
18 Nasr Structure–Activity Nasr, Annual NY Academy of Science 616:1990, Based on AIDS lecture.
75 Nogradi Stereoselective Synthesis, Weinheim; New York: VCH, 1986, 43–47.
71 Okamoto, J. of Chromotography, 1987, 389:95–102.
D26 Ohno, Organic Reactions, 37:1989.
57. O'Shea, Chirality, 1990, 257–262, 2.
17 Prince A Comparative Study Prince, B.S.E.B.M. 110:1969.
Stoner, The Resolution and Absolute . . . , Nucleosides & Nucleotides, 1993, 225–236, 12.
Scheit, Nucleotide Analogues . . . , 1980, 153–160.
Shimizu, Synthesis of Anomeric . . . , Chem. Pharm. Bull., 1967, 2011–2014, 15.
Seebach, Organic Synthesis . . . , Angew, Chem. Int. Ed. Engl., 1990, 1320–1367, 29.
Shealy, Carbocyclic Analogues . . . , J.Med. Chem., 1983, 156–161, 26.
Wainer, Drug Analysis . . . , Stevenson Chiral Separations, 1988, 11–21.
Sih, Topics in Stereochemistry, 1989.
Townsend (ed), Chemistry of Nucleosides and Nucleotides 1988.
Vince, Resolution . . . , Biochem. Biophys. Res. Comm., 1990, 912–916, 168.
Wainer, Proposal for . . . , trends in analytical chem., 1987, 125–134, 6.
Wainer, A Practical . . . , 1988, 1–38.
Wainer, Drug Stereochemistry, 1988.
Wilen, Tables of Resolving Agents and Optical Resolutions, 1972.
Wilen Resolving Agents.
Walker, "Nucleosides" in Comprehensive Chemistry: The Synthesis and Reactions of Organic Compounds 1979.
Whitesides, Chem. Int.Ed.Engl., 24:8 1985.
Haslam, Comprehensive Organic Chemistry . . . , 1979, 95–100, Pergamon Press, New York, USA.
Ueda, Synthesis . . . , Chemistry of Nucleosides and Nucleotides, 1–112, Plenum Press, New York.
Pirkle, Chiral Stationary . . . , Advances in Chromo. vol 27, 1987, 73–127, Marcel Deker, NY, USA.
Brown, State of the art . . . , Advances in Chromatography, 1980, 101–139, 1980.
1982–1986 gen subject list, Chemical Abstracts, 5654CS.
1987–1991, gen subject list, Chemical Abstracts, 6982GS, 7065GS–1067GS.
March, Advanced Organic Chemistry . . . , 1977, 108–111, McGraw–Hill, New York, USA.
Macherey–Nagel Duren, Catalog for The Separation of chiral molecule . . . .
Daicel Chemical Industries, Application Guide for chiral column . . . , 1989.
Alltech Associates, Inc., The Separation of Optical Isomers, Bulletin #87.
Daicel Chemical Industries, Crownpak, Chiralpak . . . , Catralogue.
Published abstract together with a transcript of an oral presentation given by Bernard Belleau at the 5th International Conference on AIDS, Jun. 6, 1989, plus copies of the poster used in the presentation.
Letter of Feb. 6, 1998 from the European patent representatives acting for the patentee (Emory University) to the EPO regarding the opposed patent (European Patent Application No. 91904454.5).
Declaration of Dennis C. Liotta in respect of the Opposition by Emory University against European Patent No. 0382526 B.
Declaration of Dr. Irving Wainer in relation to the Opposition by Emory University against European Patent No. 0382526 B.
Declaration of Ian M. Mutton in relation to the Opposition by Emory University against European Patent No. 0382526 B.
Declaration of Michael John Dawson in relation to the Opposition by Emory University against European Patent No. 0382526 B.
Borthwick, et al., "Synthesis and Enzymatic Resolution of Carbocyclic 2'-Ara-Fluoro-Guanosine: A Potent New Anti-Herpetic Agent," *J. Chem. Soc. Commun.,* vol. 10. pp. 656–658 (1988).

Herdewijn, et al., "Resolution of Aristeromycin Enantiomers," *J. Med. Chem.*, 1985, vol. 28, 1385–1386.

Krenitsky, et al., "An Enzymic Synthesis of Purine D–arabinonucleosdes," *Carbohydrate Research*, Vol 97, pp. 139–146 (1981).

Mahmoudian, et al., "Enzymatic Production of Optically Pure (2'R–cis)–2'–deoxy–3'–thiacytidine (3TC, Lamivudine): A Potent Anti–HIV Agent," *Enzyme Microb. Technol.*, Sep. 1993, vol. 15, 749–755, published by the Glaxo Group Research Ltd.

Pirkle and Pochansky, "Chiral Stationary Phases for the Direct LC Separation of Enantiomers," *Advances in Chromatography*, Giddings, J.C., Grushka, E., Brown, P.R., eds.: Marcel Dekker: New York, 1987; vol. 27, Chap. 3, pp. 73–127.

Secrist, et al., "Resolution of Racemic Carbocyclic Analogues of Purine Nucleosides Through the Action of Adenosine Deaminase Antiviral Activity of the Carbocyclic 2'–Deoxyguanosine Enantimers," *J. Med. Chem.*, vol. 30, pp. 746–749 (1987).

* cited by examiner

METHOD OF RESOLUTION AND ANTIVIRAL ACTIVITY OF 1,3-OXATHIOLANE NUCLESOSIDE ENANTIOMERS

This application is a continuation of application U.S. Ser. No. 08/092,248, filed on Jul. 15, 1993, now abandoned, which is a continuation of U.S. Ser. No. 07/736,089, filed on Jul. 26, 1991, now abandoned, which is a continuation-in-part of U.S. Ser. No. 07/659,760, filed on Feb. 22, 1991, now U.S. Pat. No. 5,210,085, which is a continuation-in-part of U.S. Ser. No. 07/473,318, filed on Feb. 1, 1990, now U.S. Pat. No. 5,204,466.

U.S. Government has rights in this invention arising out of the partial funding of work leading to this invention through the National Institutes of Health Grant Nos. NIH 5-21935 and NIH AI-26055, as well as a Veteran's Administration Merit Review Award.

BACKGROUND OF THE INVENTION

This invention is in the area of biologically active nucleosides, and specifically includes a method for the resolution of nucleoside enantiomers, including 1,3-oxathiolane nucleosides, and antiviral compositions that include the enantiomerically enriched 1,3-oxathiolane nucleosides, (−) and (+)-2-hydroxymethyl-5-(5-fluorocytosin-1-yl)-1,3-oxathiolane ("FTC").

This application is a continuation-in-part application of U.S. Ser. No. 07/659,760, entitled "Method for the Synthesis, Compositions and Use of 2'-Deoxy-5-Fluoro-3'-Thiacytidine and Related Compounds", filed on Feb. 22, 1991, by Dennis C. Liotta, Raymond Schinazi, and Woo-Baeg Choi, that is a continuation-in-part application of U.S. Ser. No. 07/473,318, entitled "Method and Compositions for the Synthesis of BCH-189 and Related Compounds," filed on Feb. 1, 1990, by Dennis C. Liotta and Woo-Baeg Choi.

In 1981, acquired immune deficiency syndrome (AIDS) was identified as a disease that severely compromises the human immune system, and that almost without exception leads to death. In 1983, the etiological cause of AIDS was determined to be the human immunodeficiency virus (HIV). In December, 1990, the World Health Organization estimated that between 8 and 10 million people worldwide were infected with HIV, and of that number, between 1,000,000 and 1,400,000 were in the U.S.

In 1985, it was reported that the synthetic nucleoside 3'-azido-3'-deoxythymidine (AZT) inhibits the replication of human immunodeficiency virus type 1. Since then, a number of other synthetic nucleosides, including 2',3'-dideoxyinosine (DDI), 2',3'-dideoxycytidine (DDC), 3'-fluoro-3'-deoxythymidine (FLT), 2',3'-dideoxy-2',3'-didehydrothymidine (D4T), and 3'-azido-2',3'-dideoxyuridine (AZDU), have been proven to be effective against HIV. A number of other 2',3'-dideoxynucleosides have been demonstrated to inhibit the growth of a variety of other viruses in vitro. It appears that, after cellular phosphorylation to the 5'-triphosphate by cellular kinases, these synthetic nucleosides are incorporated into a growing strand of viral DNA, causing chain termination due to the absence of the 3'-hydroxyl group.

In its triphosphate form, 3'-azido-3'-deoxythymidine is a potent inhibitor of HIV reverse transcriptase and has been approved by the FDA for the treatment of AIDS. However, the benefits of AZT must be weighed against the severe adverse reactions of bone marrow suppression, nausea, myalgia, insomnia, severe headaches, anemia, peripheral neuropathy, and seizures. These adverse side effects often occur immediately after treatment begins, whereas a minimum of six weeks of therapy is necessary to realize AZT's benefits. DDI, which has recently been approved by an FDA Committee for the treatment of AIDS, is also associated with a number of side effects, including sporadic pancreatis and peripheral neuropathy.

Both DDC and D4T are potent inhibitors of HIV replication with activities comparable (D4T) or superior (DDC) to AZT. However, both DDC and D4T are not efficiently converted to the corresponding 5'-triphosphates in vivo. Both compounds are also toxic and can cause peripheral neuropathies in humans.

The success of various 2',3'-dideoxynucleosides in inhibiting the replication of HIV in vivo or in vitro has led a number of researchers to design and test nucleosides that substitute a heteroatom for the carbon atom at the 3'-position of the nucleoside. Norbeck, et al., disclose that (±)-1-[(2β, 4β)-2-(hydroxymethyl)-4-dioxolanyl]thymine (referred to below as (±)-dioxolane-T) exhibits a modest activity against HIV ($EC_{50}$ of 20 μm in ATH8 cells), and is not toxic to uninfected control cells at a concentration of 200 μm. *Tetrahedron Letters* 30 (46), 6246, (1989).

European Patent Application Publication No. 0 382 526 filed by IAF Biochem International, Inc. discloses a number of substituted 1,3-oxathiolanes with antiviral activity, and specifically reports that the racemic mixture (about the C4'-position) of the C1'-β isomer of 2-hydroxymethyl-5-(cytosin-1-yl)-1,3-oxathiolane (referred to below as (±)-BCH-189) has approximately the same activity against HIV as AZT, and no cellular toxicity at therapeutic levels. (±)-BCH-189 has also been found to inhibit the replication of AZT-resistant, HIV isolates from patients who have been treated with AZT for longer than 36 weeks.

To market a nucleoside for pharmaceutical purposes, it must not only be efficacious with low toxicity, it must also be cost effective to manufacture. An extensive amount of research and development has been directed toward new, low cost processes for large scale nucleoside production. 2',3'-Dideoxynucleosides are currently prepared by either of two routes: derivatization of an intact nucleoside or condensation of a derivatized sugar moiety with a heterocyclic base. Although there are numerous disadvantages associated with obtaining new nucleoside analogues by modifying intact nucleosides, a major advantage of this approach is that the appropriate absolute stereochemistry has already been set by nature. However, this approach cannot be used in the production of nucleosides that contain either nonnaturally occurring bases or nonnaturally occurring carbohydrate moieties (and which therefore are not prepared from intact nucleosides), such as 1,3-oxathiolane nucleosides and 1,3-dioxolane nucleosides.

When condensing a carbohydrate or carbohydrate-like moiety with a heterocyclic base to form a synthetic nucleoside, a nucleoside is produced that has two chiral centers (at the C1' and C4'-positions), and thus exists as a diasteromeric pair. Each diastereomer exists as a set of enantiomers. Therefore, the product is a mixture of four enantiomers.

It is often found that nucleosides with nonnaturally-occurring stereochemistry in either the C1' or the C4'-positions are less active than the same nucleoside with the stereochemistry as set by nature. For example, Carter, et al., have reported that the concentration of the (−)-enantiomer of carbovir (2',3'-didehydro-2',3'-dideoxyguanosine) required to reduce the reverse transcriptase activity by 50% ($EC_{50}$)

is 0.8 µM, whereas the $EC_{50}$ for the (+)-enantiomer of carbovir is greater than 60 µM. *Antimicrobial Agents and Chemotherapy*, 34:6, 1297–1300 (June 1990).

U.S. Ser. No. 07/659,760 discloses that 1,3-oxathiolane and 1,3-dioxolane nucleosides can be prepared with high diastereoselectivity (high percentage of nucleoside with a β configuration of the bond from the C1'-carbon to the heterocyclic base) by careful selection of the Lewis acid used in the condensation process. It was discovered that condensation of a 1,3-oxathiolane nucleoside with a base occurs with almost complete β-stereospecificity when stannic chloride is used as the condensation catalyst, and condensation of 1,3-dioxolane with a base occurs with almost complete β-stereospecificity when various chlorotitanium catalysts are employed. Other Lewis acids provide low (or no) C1'-β selectivity or simply fail to catalyze the reactions.

There remains a strong need to provide a cost effective, commercially viable method to obtain β-stereospecificity of synthetic nucleosides prepared by condensing a carbohydrate-like moiety with a base. This is important because it is likely that many synthetic nucleoside inhibitors of viral replication now emerging from academic and commercial laboratories will require resolution. An economical and facile method for resolving racemic mixtures of nucleosides would greatly facilitate antiviral research and ultimately, commercial manufacture. Further, resolution of racemic mixtures of nucleosides may provide a route to increase the activity of synthetic nucleosides by eliminating or minimizing the undesired enantiomer.

Therefore, it is an object of the present invention to provide a method for the resolution of racemic mixtures of nucleosides.

It is another object of the present invention to provide enantiomerically enriched 1,3-oxathiolane nucleosides.

It is still another object of the present invention to provide enantiomerically enriched 1,3-oxathiolane nucleosides with significant antiviral activity and low toxicity.

SUMMARY OF THE INVENTION

A process for the resolution of a racemic mixture of nucleoside enantiomers or their derivatives is disclosed that includes the step of exposing the racemic mixture to an enzyme that preferentially catalyzes a reaction in one of the enantiomers. The process can be used to resolve a wide variety of nucleosides, including pyrimidine and purine nucleosides that are optionally substituted in the carbohydrate moiety or base moiety. The process can also be used to resolve nucleoside derivatives that contain additional heteroatoms in the carbohydrate moiety, for example, FTC and BCH-189. The resolution of nucleosides can be performed on large scale at moderate cost.

It has been discovered that the nucleoside enantiomer (−) 2-hydroxymethyl-5-(5-fluorocytosin-1-yl)-1,3-oxathiolane ("FTC") exhibits significant activity against HIV ($EC_{50}$ of 0.0077 to 0.02 µM), HBV (hepatitis B virus), and other viruses replicating in a similar manner. The (+)-enantiomer of FTC is also active against HIV ($EC_{50}$ of 0.28–0.84 µM).

DETAILED DESCRIPTION OF THE INVENTION

Figure 1:
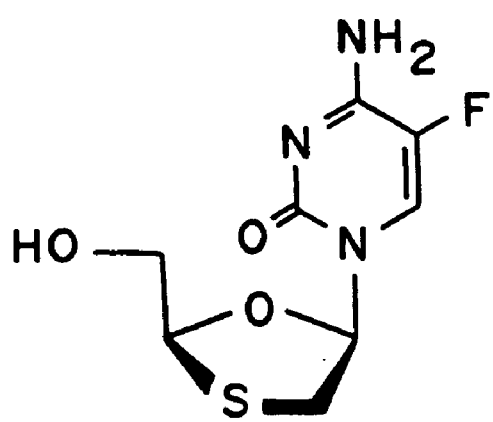
FIG. 1 is an illustration of the chemical structure of 2-hydroxymethyl-5-(5-fluorocytosin-1-yl)-1,3-oxathiolane ("FTC").
Figure 2:
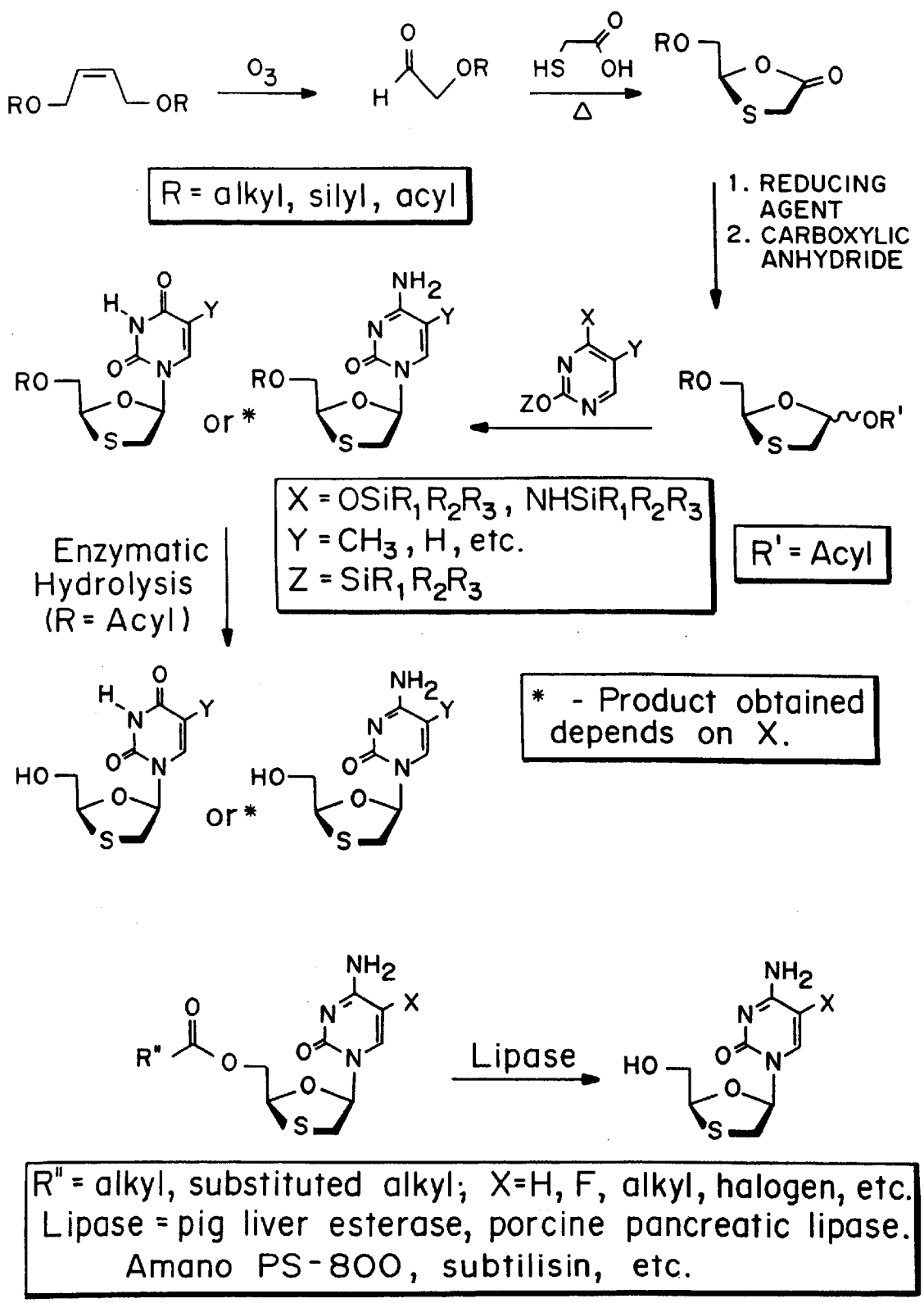
FIG. 2 is an illustration of a method for the preparation of enantiomerically enriched cytidine and uridine 1,3-oxathiolane nucleosides.

As used herein, the term "enantiomerically enriched nucleoside" refers to a nucleoside composition that includes at least 95% of a single enantiomer of that nucleoside.

As used herein, the term BCH-189 refers to 2-hydroxymethyl-5-(cytosin-1-yl)-1,3-oxathiolane.

As used herein, the term FTC refers to 2-hydroxymethyl-5-(5-fluorocytosin-1-yl)-1,3-oxathiolane.

As used herein, the term "preferential enzyme catalysis" refers to catalysis by an enzyme that favors one substrate over another.

I. Resolution of Racemic Mixtures of Nucleosides During the Hydrolysis

A method is provided for the resolution of racemic mixtures of nucleoside enantiomers. The method involves the use of an enzyme that preferentially catalyzes a reaction of one enantiomer in a racemic mixture. The reacted enantiomer is separated from the unreacted enantiomer on the basis of the new difference in physical structure. Given the disclosure herein, one of skill in the art will be able to choose an enzyme that is selective for the nucleoside enantiomer of choice (or selective for the undesired enantiomer, as a method of eliminating it), by selecting of one of the enzymes discussed below or by systematic evaluation of other known enzymes. Given this disclosure, one of skill in the art will also know how to modify the substrate as necessary to attain the desired resolution. Through the use of either chiral NMR shift reagents, polarimetry, or chiral HPLC, the optical enrichment of the recovered ester can be determined.

The following examples further illustrate the use of enzymes to resolve racemic mixtures of enantiomers. Other known methods of resolution of racemic mixtures can be used in combination with the method of resolution disclosed herein. All of these modifications are considered within the scope of the invention.

Resolution Based on Hydrolysis of C5'-Nucleoside Esters

In one embodiment, the method includes reacting the C5'-hydroxyl group of a mixture of nucleoside racemates with an acyl compound to form C5'-esters in which the nucleoside is in the "carbinol" end of the ester. The racemic mixture of nucleoside C5'-esters is then treated with an enzyme that preferentially cleaves, or hydrolyses, one of the enantiomers and not the other.

An advantage of this method is that it can be used to resolve a wide variety of nucleosides, including pyrimidine and purine nucleosides that are optionally substituted in the carbohydrate moiety or base moiety. The method can also be used to resolve nucleoside derivatives that contain additional heteroatoms in the carbohydrate moiety, for example, FTC and BCH-189. The broad applicability of this method resides in part on the fact that although the carbinol portion of the ester plays a role in the ability of an enzyme to differentiate enantiomers, the major recognition site for these enzymes is in the carboxylic acid portion of the ester. Further, one may be able to successfully extrapolate the results of one enzyme/substrate study to another, seemingly-different system, provided that the carboxylic acid portions of the two substrates are the same or substantially similar.

Another advantage of this method is that it is regioselective. Enzymes that hydrolyse esters typically do not catalyze extraneous reactions in other portions of the molecule. For example, the enzyme lipase catalyses the hydrolysis of the ester of 2-hydroxymethyl-5-oxo-1,3-oxathiolane without hydrolysing the internal lactone. This contrasts markedly with "chemical" approaches to ester hydrolysis.

Still another advantage of this method is that the separation of the unhydrolysed enantiomer and the hydrolysed enantiomer from the reaction mixture is quite simple. The unhydrolysed enantiomer is more lipophilic than the hydrolysed enantiomer and can be efficiently recovered by simple extraction with one of a wide variety of nonpolar organic solvents or solvent mixtures, including hexane and hexane/ether. The less lipophilic, more polar hydrolysed enantiomer can then be obtained by extraction with a more polar organic solvent, for example, ethyl acetate, or by lyophilization, followed by extraction with ethanol or methanol. Alcohol should be avoided during the hydrolysis because it can denature enzymes under certain conditions.

Enzymes and Substrates

With the proper matching of enzyme and substrate, conditions can be established for the isolation of either nucleoside enantiomer. The desired enantiomer can be isolated by treatment of the racemic mixture with an enzyme that hydrolyses the desired enantiomer (followed by extraction of the polar hydrolysate with a polar solvent) or by treatment with an enzyme that hydrolyses the undesired, enantiomer (followed by removal of the undesired enantiomer with a nonpolar solvent).

Enzymes that catalyze the hydrolysis of esters include esterases, for example pig liver esterase, lipases, including porcine pancreatic lipase and Amano PS-800 lipase, substillisin, and α-chymotrypsin.

The most effective acyl group to be used to esterify the C5'-position of the nucleoside can be determined without undue experimentation by evaluation of a number of homologs using the selected enzyme system. For example, when 1,3-oxathiolane nucleosides are esterified with butyric acid, resolutions with both pig liver esterase and Amano PS-800 proceed with high enantioselectivity (94–100 enantiomeric excess) and opposite selectivity. Non-limiting examples of other acyl groups that can be evaluated for use with a particular nucleoside enantiomeric mixture and particular enzyme include alkyl carboxylic acids and substituted alkyl carboxylic acids, including acetic acid, propionic acid, butyric acid, and pentanoic acid. With certain enzymes, it may be preferred to use an acyl compound that is significantly electron-withdrawing to facilitate hydrolysis by weakening the ester bond. Examples of electron-withdrawing acyl groups include α-haloesters such as 2-chloropropionic acid, 2-chlorobutyric acid, and 2-chloropentanoic acid. α-Haloesters are excellent substrates for lipases.

Resolution Conditions

The enzymatic hydrolyses are typically carried out with a catalytic amount of the enzyme in an aqueous buffer that has a pH that is close to the optimum pH for the enzyme in question. As the reaction proceeds, the pH drops as a result of liberated carboxylic acid. Aqueous base should be added to maintain the pH near the optimum value for the enzyme. The progress of the reaction can be easily determined by monitoring the change in pH and the amount of base needed to maintain pH. The hydrophobic ester (the unhydrolysed enantiomer) and the more polar alcohol (the hydrolysed enantiomer) can be sequentially and selectively extracted from the solution by the judicious choice of organic solvents. Alternatively, the material to be resolved can be passed through a column that contains the enzyme immobilized on a solid support.

Enzymatic hydrolyses performed under heterogeneous conditions can suffer from poor reproducibility. Therefore, it is preferred that the hydrolysis be performed under homogeneous conditions. Alcohol solvents are not preferred because they can denature the enzymes. Homogeneity can be achieved through the use of non-ionic surfactants, such as Triton X-100. However, addition of these surfactants not only assists in dissolving the starting material, they also enhance the aqueous solubility of the product. Therefore, although the enzymatic reaction can proceed more effectively with the addition of a non-ionic surfactant than under heterogeneous conditions, the isolation of both the recovered starting material and the product can be made more difficult. The product can be isolated with appropriate chromatographic and chemical (e.g., selective salt formation) techniques. Diacylated nucleosides can be used but are often quite lipophilic and hard to dissolve in the medium used.

EXAMPLE 1

Enantioselective Lipase-Catalyzed Hydrolysis of FTC Esters

A number of 5'-O-acyl derivatives of FTC were prepared by selective O-acylation of the N-hydrochloride salt (see Table 1) of (±)-FTC. The efficiency of the hydrolysis of the derivatives by lipases was investigated. As shown in Table 1, pig liver esterase (PLE) exhibits a high level of selectivity for the hydrolysis of the ester of the (+)-enantiomer of FTC. In contrast, PS-800 hydrolyses the ester of the (−)-enantiomer of FTC preferentially. The rate of the hydrolysis was also found to be dependent on the nature of the acyl group; the acetyl derivative was significantly slower than the butyryl derivative. It has now been discovered that the rate of the hydrolysis of the propionic acid ester of FTC is even faster than that observed for the butyrate derivative. % Recovery and % ee were both determined using HPLC. Although the enantioselectivity is excellent when employing PLE (typically 97% e.e. or higher), additional enrichment can be accomplished by sequential enzymatic hydrolysis reactions in which the enantiomerically-enriched butyrate from a PLE-catalyzed hydrolysis is subjected to enzymatic hydrolysis by PS-800.

TABLE 1

Comparison of Effect of Ester on Enzyme Hydrolysis.

| substrate | % recovery | % e.e. (s.m.) |
|---|---|---|
| FTC Esters with PLE: | | |
| acetate | 32.68 | N.D. |
| propionate | 39.87 | N.D. |
| butyrate | 48.00 | 98 |
| butyrate | 45.71 | 98.6 |
| FTC Esters with PS800: | | |
| acetate | 73.17 | N.D. |
| propionate | 52.67 | N.D. |
| butyrate | 58.34 | N.D. |
| valerate | 41.50 | 94 |

EXAMPLE 2

Figure 3:
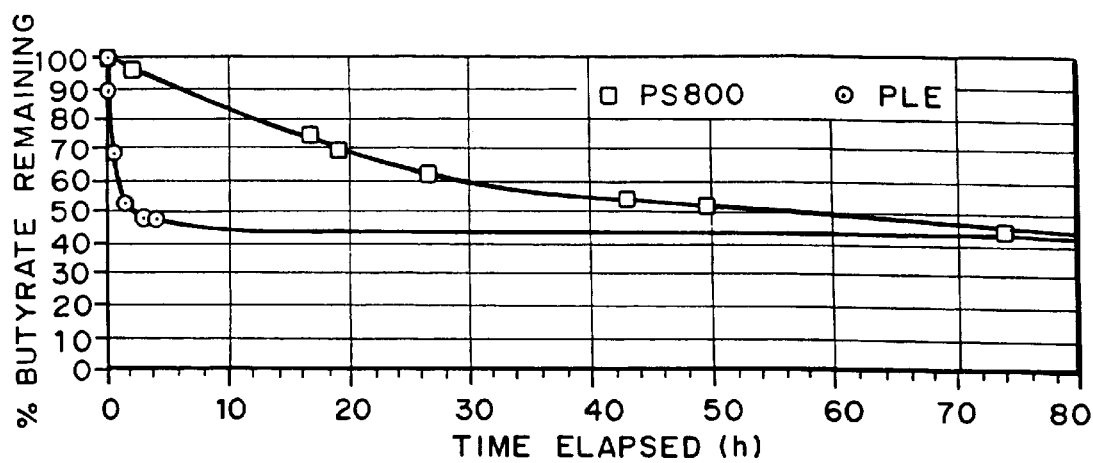
FIG. 3 is a graph indicating the progress of lipase-catalyzed hydrolysis of the 5'-butyryl ester of FTC over time using the enzymes PS800 (-open square-) and PLE (-open circle with dot-).

Procedure for the Preparation of (+)- and (−)-FTC via Enantioselective, Lipase-Catalyzed Hydrolysis of FTC Butyrate The 5′-O-butyrate of (±)-FTC (1) (0.47 mmol, 149 mg) was dissolved in 16 mL of a solution of 4:1 pH 8 buffer:$CH_3CN$. The clear solution was stirred and treated with 26 mg of pig liver esterase (PLE-A). The progress of the reaction was monitored by HPLC (FIG. 3). After 20 hours (52% conversion), the reaction mixture was extracted with 2×80 mL of $CHCl_3$ and 80 mL of ethyl acetate. The organic layer extracts were combined, dried over anhydrous $MgSO_4$, filtered, and concentrated by rotary evaporation. The resulting residue was eluted on 2×1000 m pTLC plates using ethyl acetate as eluant (double elution) to give, after isolation, 53 mg (36% based on starting material) of FTC butyrate which was determined to have 98% enantiomeric excess (e.e.) by HPLC analysis. The enantiomerically-enriched butyrate was then treated with 1.6 mL of methanol followed by 0.38 mmol (20 mg) of sodium methoxide. The resulting mixture was stirred at room temperature, and the progress of the reaction was monitored by HPLC. The reaction was completed within 30 minutes. The solvent was removed by rotary evaporation to give a crude white solid (76 mg) that was eluted on a 1000 m pTLC using 5:1 ethyl acetate:ethanol. (−)-FTC was isolated as a white solid (33 mg; 82% yield). HPLC analysis of the FTC as its 5′-O-acetate derivative showed 97% e.e.; $[\alpha](^{20}{}_D)$ −120.5°(c =0.88; abs. ethanol).

Similarly, 1.2 mmol (375 mg) of the 5′-O-butyrate of (+)-FTC was dissolved in 40 mL of 4:1 pH 8 buffer-$CH_3CN$. The clear solution was stirred and treated with 58 mg of pig liver esterase (PLE-A). The progress of the reaction was monitored by HPLC. After 90 minutes (38% conversion), the reaction mixture was added to 150 mL of CHCl. The layers were separated and the aqueous layer lyophilized to remove solvent. The white residue from the lyophilization was extracted with 3×10 mL of absolute ethanol. The extracts were filtered, combined, and concentrated in vacuo to yield 179 mg of crude oil. The crude material was eluted on a 45×30 mm column of silica gel using 3×75 mL of ethyl acetate followed by 5:1 ethyl acetate-ethanol. (+)-FTC (a) was isolated as a white solid (109 mg; 37% based on starting butyrate). HPLC analysis of the (+)-FTC as its 5′-O-acetate derivative showed 97.4% e.e.; $[a]O(^{20}{}_D)$ +113.4° (c=2.53; absolute ethanol)

A similar reaction was performed using 0.12 mmol (37 mg) of the 5′-O-butyrate of FTC and 7 mg of PS-800 in 4.0 mL of 4:1 pH 8 buffer:$CH_3CN$. The reaction was considerably slower than that with PLE-A and required 74 hours for 59% conversion. The recovered butyrate (11.4 mg; 31% of the initial amount) was found to be 94% e.e. by HPLC.

Resolution of Nucleoside Enantiomers with Cytidine-Deoxycytidine Deaminase

In an alternative embodiment, cytidine-deoxycytidine deaminase is used to resolve racemic mixtures of 2-hydroxymethyl-5-(cytosin-1-yl)-1,3-oxathiolane and its derivatives, including 2-hydroxymethyl-5-(5-fluoro-cytosin-1-yl)-1,3-oxathiolane. The enzyme catalyses the deamination of the cytosine moiety to a uridine. It has been discovered that one of the enantiomers of 1,3-oxathiolane nucleosides is a preferred substrate for cytidine-deoxycytidine deaminase. The enantiomer that is not converted to a uridine (and therefore is still basic) is extracted from the solution with an acidic solution. Care should be taken to avoid strong acidic solutions (pH below 3.0), that may cleave the oxathiolane ring.

Cytidine-deoxycytidine deaminase can be isolated from rat liver or human liver, or expressed from recombinant sequences in procaryotic system such as in *E. coli*.

The method of resolution of cytidine nucleoside enantiomers using cytidine-deoxycytidine deaminase can be used as the sole method of resolution or can be used in combination with other methods of resolution, including resolution by enzymatic hydrolysis of 5′-O-nucleoside esters as described above.

Combination of Enzymatic Resolution with Classical Resolution Methods

The process described above for resolving racemic mixtures of nucleoside enantiomers can be combined with other classical methods of enantiomeric resolution to increase the optical purity of the final product.

Classical methods of resolution include a variety of physical and chemical techniques. Often the simplest and most efficient technique is recrystallization, based on the principle that racemates are often more soluble than the corresponding individual enantiomers. Recrystallization can be performed at any stage, including on the acylated compounds and or the final enantiomeric product. If successful, this simple approach represents a method of choice.

When recrystallization fails to provide material of acceptable optical purity, other methods can be evaluated. If the nucleoside is basic (for example, a cytidine) one can use chiral acids that form diastereomeric mixtures that may possess significantly different solubility properties. Nonlimiting examples of chiral acids include malic acid, mandelic acid, dibenzoyl tartaric acid, 3-bromocamphor-8-sulfonic acid, 10-camphorsulfonic acid, and di-p-toluoyltartaric acid. Similarly, acylation of the free hydroxyl group with a chiral acid derivative also results in the formation of diastereomeric mixtures whose physical properties may differ sufficiently to permit separation.

Small amounts of enantiomerically enriched nucleosides can be obtained or purified by passing the racemic mixture through an HPLC column that has been designed for chiral separations, including cyclodextrin bonded columns marketed by Rainin Corporation.

EXAMPLE 3

Separation of Racemic Mixtures of Nucleosides by HPLC

The resolutions of the C4'-enantiomers of (±)-BCH-189 and (±)-FTC were performed using a chiral cyclodextrin bonded (cyclobond AC-I) column obtained from Rainin Corporation (Woburn, Mass.). The conditions were as follows: Isocratic 0.5% methanol in water; flow rate 1 ml/min., UV detection at 262 nm. HPLC grade methanol was obtained from J. T. Baker (Phillipsburg, N.J.). The racemic mixtures were injected and fractions were collected. Fractions containing each of the enantiomers were pooled, frozen, and then lyophilized. The compounds were characterized by UV spectroscopy and by their retention times on HPLC. In general, the (−)-enantiomers have lower retention times than the (+)-enantiomers (see *J. Liquid Chromatography* 7:353–376, 1984). The concentrations of the compounds were determined by UV spectroscopy, using a stock solution of known concentration (15 $\mu$M) prepared in water for biological evaluation. The retention times for the separated enantiomers are provided in Table 2.

TABLE 2

Retention Times of Enantiomers of BCH-189 and FTC

| Compound | $R_t$ (min) |
|---|---|
| (−)-BCH-189 | 9.0 |
| (+)-BCH-189 | 10.0 |
| (−)-FTC | 8.3 |
| (+)-FTC | 8.7 |

II. Antiviral Activity of 2-Hydroxymethyl-5-(5-Fluorocytosin-1-yl)-1,3-oxathiolane ("FTC")

It is often desirable to screen a number of racemic mixtures of nucleosides as a preliminary step to determine which warrant further resolution into enantiomerically enriched components and evaluation of antiviral activity. The ability of nucleosides to inhibit HIV can be measured by various experimental techniques. The technique used herein, and described in detail below, measures the inhibition of viral replication in phytohemagglutinin (PHA) stimulated human peripheral blood mononuclear (PBM) cells infected with HIV-1 (strain LAV). The amount of virus produced is determined by measuring the virus-coded reverse transcriptase enzyme. The amount of enzyme produced is proportional to the amount of virus produced. Table 4 provides the $EC_{50}$ values (concentration of nucleoside that inhibits the replication of the virus by 50% in PBM cells) and $IC_{50}$ values (concentration of nucleoside that inhibits 50% of the growth of mitogen-stimulated uninfected human PBM cells) of a number of (±)-1,3-oxathiolane and nucleosides.

EXAMPLE 4

Anti-HIV activity of (±)-1,3-Oxathiolane Nucleosides

A. Three-day-old phytohemagglutinin-stimulated PBM cells ($10^6$ cells/ml) from hepatitis B and HIV-1 seronegative healthy donors were infected with HIV-1 (strain LAV) at a concentration of about 100 times the 50% tissue culture infectious dose (TICD 50) per ml and cultured in the presence and absence of various concentrations of antiviral compounds.

B. Approximately one hour after infection, the medium, with the compound to be tested (2 times the final concentration in medium) or without compound, was added to the flasks (5 ml; final volume 10 ml). AZT was used as a positive control.

C. The cells were exposed to the virus (about $2 \times 10^5$ dpm/ml, as determined by reverse transcriptase assay) and then placed in a $CO_2$ incubator. HIV-1 (strain LAV) was obtained from the Center for Disease Control, Atlanta, Ga. The methods used for culturing the PBM cells, harvesting the virus and determining the reverse transcriptase activity were those described by McDougal et al. (*J. Immun. Meth.* 76, 171–183, 1985) and Spira et al. (*J. Clin. Meth.* 25, 97–99, 1987), except that fungizone was not included in the medium (see Schinazi, et al., *Antimicrob. Agents Chemother.* 32, 1784–1787 (1988); Id., 34:1061–1067 (1990)).

D. On day 6, the cells and supernatant were transferred to a 15 ml tube and centrifuged at about 900 g for 10 minutes. Five ml of supernatant were removed and the virus was concentrated by centrifugation at 40,000 rpm for 30 minutes (Beckman 70.1 Ti rotor). The solubilized virus pellet was processed for determination of the levels of reverse transcriptase. Results are expressed in dpm/ml of sampled supernatant. Virus from smaller volumes of supernatant (1 ml) can also be concentrated by centrifugation prior to solubilization and determination of reverse transcriptase levels.

The median effective ($EC_{50}$) concentration was determined by the median effect method (*Antimicrob. Agents Chemother.* 30, 491–498 (1986). Briefly, the percent inhibition of virus, as determined from measurements of reverse transcriptase, is plotted versus the micromolar concentration of compound. The $EC_{50}$ is the concentration of compound at which there is a 50% inhibition of viral growth.

E. Mitogen stimulated uninfected human PBM cells ($3.8 \times 10^5$ cells/ml) were cultured in the presence and absence of drug under similar conditions as those used for the antiviral assay described above. The cells were counted after 6 days using a hemacytometer and the trypan blue exclusion method, as described by Schinazi et al., *Antimicrobial Agents and Chemotherapy*, 22(3), 499 (1982). The $IC_{50}$ is the concentration of compound which inhibits 50% of normal cell growth.

TABLE 3

$EC_{50}$ and $IC_{50}$ of Various Analogues of 1,3-Oxathiolane Nucleosides in human PBM cells.

| Code | X or Y | R | Antiviral $EC_{50}$, $\mu$M | Cytotoxicity $IC_{50}$, $\mu$M |
|---|---|---|---|---|
| DLS-009 | X = O | H | >100 | >100 |
| DLS-010 | X = O | Me | 64.4 | >100 |
| DLS-027 | X = O | F | >100 | >100 |
| DLS-028 | X = O | Cl | 60.8 | >100 |
| DLS-044 | X = O | Br | >100 | >100 |
| DLS-029 | X = O | I | >100 | >100 |
| DLS-020 | Y = $NH_2$ | H | 0.02 | >100 |
| DLS-011 | Y = $NH_2$ | Me | >10 | >100 |
| DLS-022 | Y = $NH_2$ | F | 0.011 | >100 |
| DLS-023 | Y = $NH_2$ | Cl | 38.7 | >100 |
| DLS-021 | Y = $NH_2$ | Br | 77.4 | >100 |
| DLS-026 | Y = $NH_2$ | I | 0.72 | >100 |
| DLS-058(−) | Y = $NH_2$ | F | 0.0077 | >100 |
| DLS-059(+) | Y = NH2 | F | 0.84 | >100 |
| DLS-053 | Y = $NH_2$ | $CF_3$ | 60.7 | >100 |

TABLE 3-continued

EC$_{50}$ and IC$_{50}$ of Various Analogues of 1,3-Oxathiolane Nucleosides in human PBM cells.

| Code | X or Y | R | Antiviral EC$_{50}$, μM | Cytotoxicity IC$_{50}$, μM |
|------|--------|---|-------------------------|----------------------------|

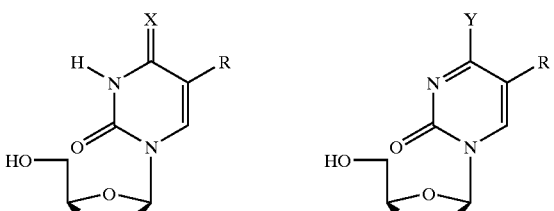

or*

As indicated in Table 3, in general, the substituted cytosine 1,3-oxathiolane nucleosides are more active than the corresponding uracil nucleosides. One of the compounds, (±)-FTC, (referred to as "DLS-022", compound 8) not only exhibited exceptional activity (approximately 10 nM in PBM cells), but also quite low toxicity (>100 μM in PBM, Vero and CEM cells). This activity compares quite favorably with 2',3'-dideoxyadenosine (DDA, EC$_{50}$=0.91 μM), 3'-azido-2',3'-dideoxyuridine (AZDU, EC$_{50}$= 0.18–0.46 μM), 3'-dideoxythymidine (DDT, EC$_{50}$=0.17 μM), and dideoxycytidine (DDC, EC$_{50}$=0.011 μM).

The IC$_{50}$ of (±)-FTC was measured as over 100 μM, indicating that the compound was not toxic in uninfected PBM cells evaluated up to 100 μM.

EXAMPLE 5

Antiviral Activity of the Enantiomers of FTC Resolved by HPLC

Figure 4:
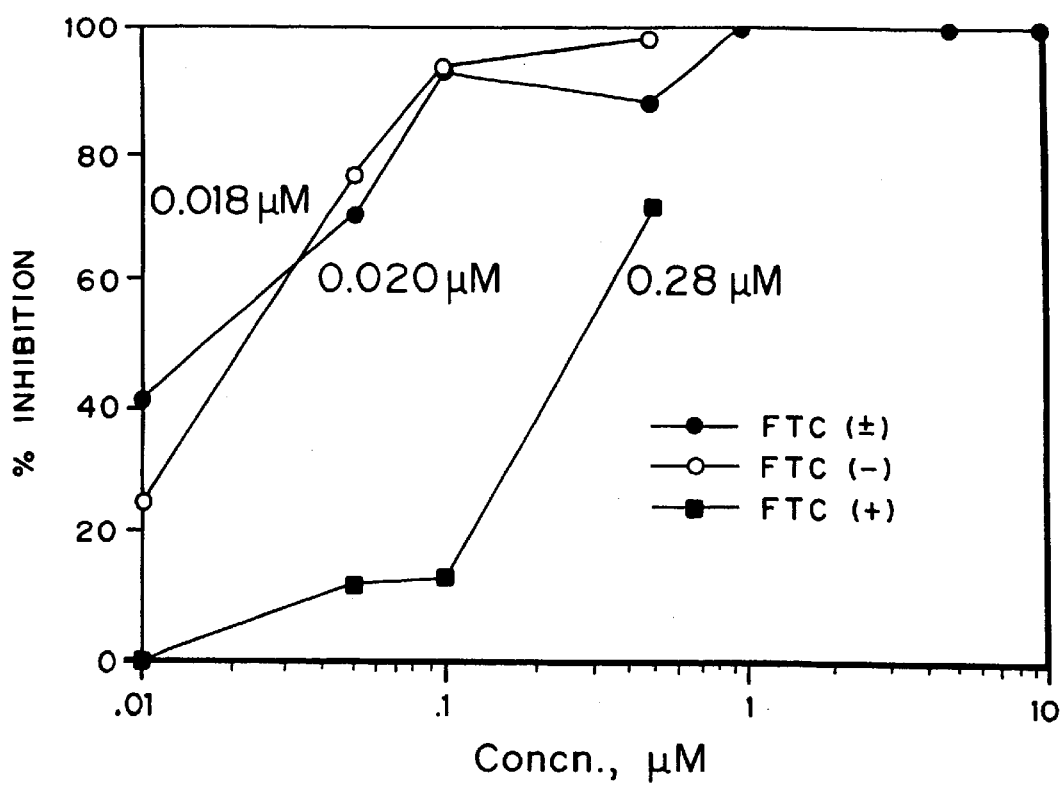
FIG. 4 is a graph of the effect of concentration (µM) of racemic and enantiomerically enriched FTC (prepared by the method of Example 3) versus the percent inhibition of human PBM cells infected with HIV-1. ((-darkened circle-, (±)-FTC), (-circle-, (−)-FTC), (-darkened square-,(+)-FTC).

The enantiomers of FTC were isolated by the method of Example 3, and the antiviral activity evaluated by the method of Example 4. The results are provided in Table 4, and illustrated in FIG. 4.

TABLE 4

Antiviral Activity of the (+) and (−) Enantiomers of FTC

| Treatment | Concn., μM | DPM/ml | % Inhibition (Corrected) | EC$_{50}$:μM |
|-----------|-----------|--------|--------------------------|--------------|
| FTC (±) | 0.0001 | 73,755 | 26.6 | 0.018 |
|  | 0.005 | 83,005 | 16.3 |  |
|  | 0.01 | 60,465 | 41.3 |  |
|  | 0.05 | 34,120 | 70.4 |  |
|  | 0.1 | 14,160 | 92.4 |  |
|  | 0.5 | 18,095 | 88.1 |  |
|  | 1 | 7,555 | 99.7 |  |
|  | 5 | 7,940 | 99.3 |  |
|  | 10 | 5,810 | 101.7 |  |
| FTC (−) | 0.001 | 76,275 | 23.8 | 0.02 |
|  | 0.005 | 58,590 | 43.3 |  |
|  | 0.01 | 75,350 | 24.8 |  |
|  | 0.05 | 28,890 | 76.2 |  |
|  | 0.1 | 13,175 | 93.5 |  |
|  | 0.5 | 9,485 | 97.6 |  |
| FTC (+) | 0.001 | 94,340 | 3.8 | 0.28 |
|  | 0.005 | 107,430 | −10.6 |  |
|  | 0.01 | 99,465 | −1.8 |  |
|  | 0.05 | 87,120 | 11.8 |  |
|  | 0.1 | 86,340 | 12.7 |  |
|  | 0.5 | 33,225 | 71.4 |  |

As indicated in Table 4, the (−)-enantiomer of FTC is approximately one order of magnitude more potent than the (+)-FTC enantiomer, and has approximately the same anti-HIV activity as the racemic mixture. Neither the enantiomers nor the racemic mixture is toxic up to 100 μM as measured by Trypan Blue exclusion in human PBM cels.

EXAMPLE 6

Antiviral Activity of Enantiomers Resolved by Method of Example 2

Figure 5:
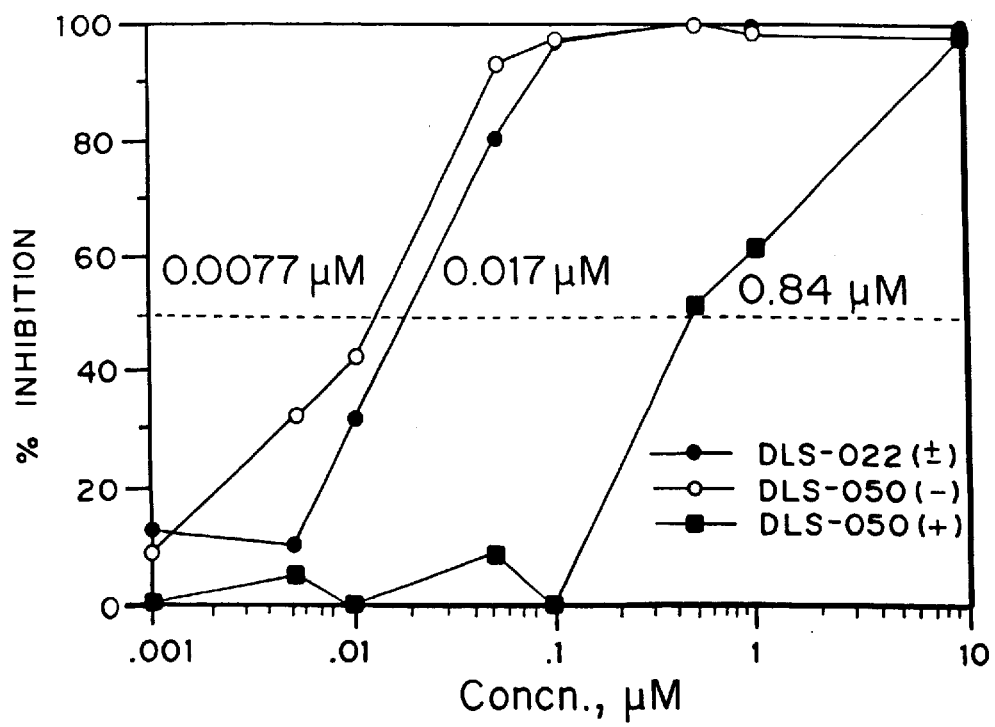
FIG. 5 is a graph of the effect of concentration (µM) of racemic and enantiomerically enriched FTC (prepared by method of Example 2) on the percent inhibition of human PBM cells infected with HIV-1. ((-darkened circle-, (±)-FTC), (-circle -,(−)-FTC), (-darkened square-,(+)-FTC).

The enantiomers of (±)-FTC were also resolved by the method of Example 2, and the antiviral activity evaluated by the method of Example 4. The results are illustrated in FIG. 5. As indicated in FIG. 5, the EC$_{50}$ of the racemic mixture of FTC was measured at 0.017 μM, the EC$_{50}$ of (−)-FTC at 0.0077 μM, and the EC$_{50}$ of (+)-FTC at 0.84 μM.

The differences in EC$_{50}$s as measured in Examples 5 and 6 may be due to a number of factors, including differences in donor PBM cells, the inherent error of the anti-HIV screening procedure (estimated at approximately 10%), and differences in the measurement of concentration of the nucleosides as resolved in the methods of Examples 2 and 3. In the method of Example 2, the FTC enantiomers were isolated as solids and weighed to prepare the testing solution. In the method of Example 3, the concentration of the FTC enantiomers was estimated from UV absorption measurements.

The data indicates that the (+) enantiomer is significantly less potent than the (−) entantiomer or the racemic mixture.

EXAMPLE 7

Antiviral Activity of the Enantiomers of BCH-189 Resolved by HPLC

Figure 6:
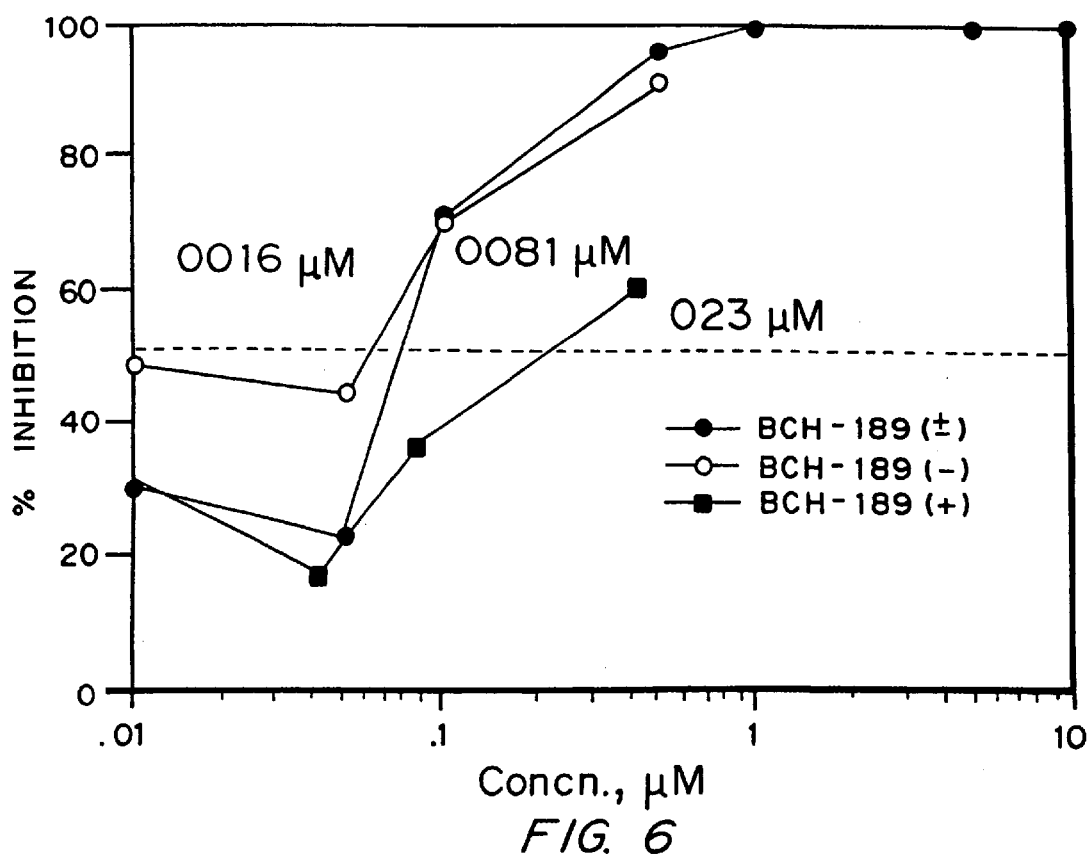
FIG. 6 is a graph of the effect of concentration (µM) of racemic and enantiomerically enriched BCH-189 (prepared by the method of Example 3) on the percent inhibition of human PBM cells infected with HIV-1. ((-darkened circle-, (±)-BCH-189), (-circle-, (−)-BCH-189), (-darkened square-, (+)-BCH-189).

The enantiomers of BCH-189 were isolated by the method of Example 3, and the antiviral activity evaluated by the method of Example 4. The results are provided in Table 5, and illustrated in FIG. 6.

TABLE 5

Antiviral Activity of the (+) and (−) Enantiomers of BCH-189

| Treatment | Concn., μM | DPM/ml | % Inhibition (Corrected) | EC$_{50}$:μM |
|-----------|-----------|--------|--------------------------|--------------|
| Blanks | mean | 762 |  |  |
| HIV Std. |  | 158,705 |  |  |
| Uninfected | mean | 7,320 |  |  |
| Control | ±SD | 4,520 |  |  |
| Infected | mean | 97,795 |  |  |
| Control | ±SD | 6,790 |  |  |
| BCH-189 (±) | 0.001 | 65,170 | 36.1 | 0.081 |
|  | 0.005 | 62,595 | 38.9 |  |
|  | 0.01 | 70,875 | 29.8 |  |
|  | 0.05 | 77,650 | 22.3 |  |
|  | 0.1 | 33,165 | 71.4 |  |
|  | 0.5 | 10,765 | 96.2 |  |
|  | 1 | 7,745 | 99.5 |  |
|  | 5 | 6,800 | 100.6 |  |
|  | 10 | 4,470 | 103.2 |  |
| BCH-189 (−) | 0.001 | 76,400 | 23.6 | 0.016 |
|  | 0.005 | 66,875 | 34.2 |  |
|  | 0.01 | 54,170 | 48.2 |  |
|  | 0.05 | 57,615 | 44.4 |  |
|  | 0.1 | 34,705 | 69.7 |  |
|  | 0.5 | 15,250 | 91.2 |  |
| BCH-189 (+) | 0.00085 | 71,795 | 28.7 | 0.23 |
|  | 0.00425 | 99,710 | −2.1 |  |
|  | 0.0085 | 68,355 | 32.5 |  |
|  | 0.0415 | 82,845 | 16.5 |  |
|  | 0.0825 | 65,100 | 36.1 |  |
|  | 0.412 | 43,260 | 60.3 |  |

As indicated in Table 6, the (−)-enantiomer of BCH-189 is approximately one order of magnitude more potent than the (+)-FTC enantiomer, and has approximately the same anti-HIV activity as the racemic mixture. Neither enantiomer exhibited any toxicity in a concentration up to 100 μM as measured by Trypan Blue exclusion in human PBM cells.

EXAMPLE 8

Uptake of (±)-FTC Into Human PBM Cells

Studies were undertaken using radiolabeled agent in order to follow the intracellular profiles of the parent drug and metabolites detected within the cell. All studies were conducted in duplicate. Human peripheral blood mononuclear cells (PBM cells) are suspended in RPMI 1640 medium containing 10% getal calf serum and antibiotics (2×10"cells/ml), 10 ml per timepoint) and incubated with addition of 10 μM FTC (specific ctivity about 700 dpm/pmol). Cells are exposed to the drug for 2, 6, 12 and 24 hours. At these timepoints, the medium is removed and the cells are washed two times with cold Hank's balanced salt solution. Extraction is performed with addition of 0.2 ml of 60% cold methanol/water and stored overnight at −70° C. The following morning, the suspensions are centrifuged and extractions are repeated two times for 0.5 hours at −70° C. The total supernatants (0.6 ml) are lyophilized to dryness. The residues are resuspended in 250 μl of water and aliquots comprising between 50 and 100 μl are analyzed by HPLC. Quantitation of intracellular parent drug and metabolic derivatives are conducted by HPLC. Because of the potential acid lability of some compounds, a buffer system close to physiological pH is used for the separation of the metabolites.

Figure 7:
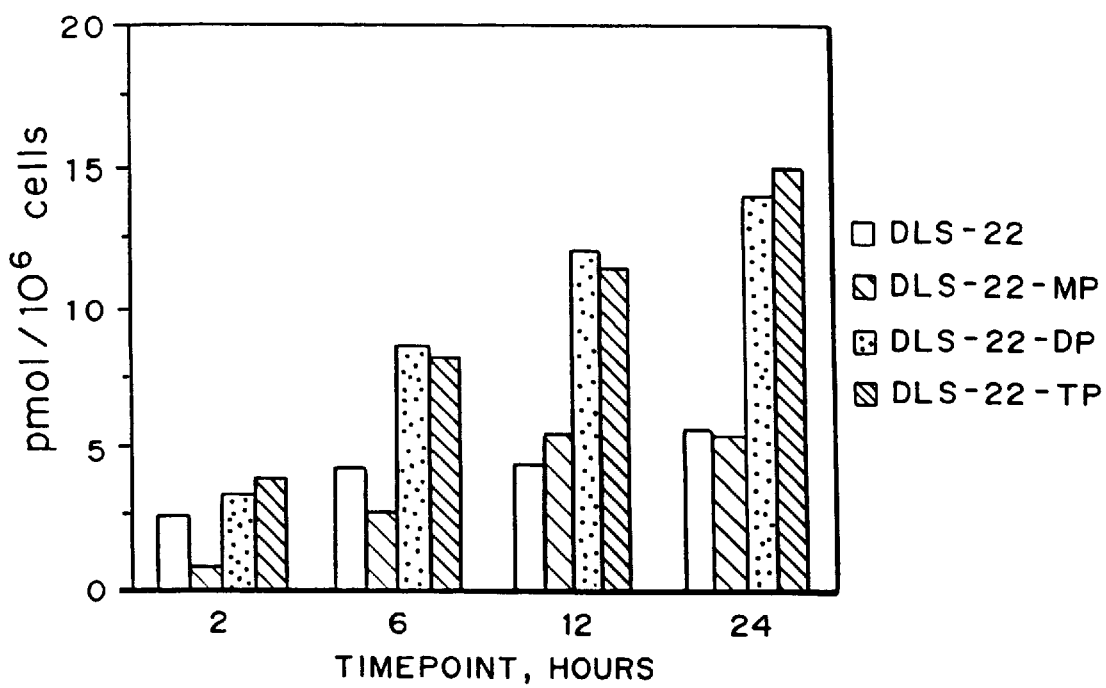
FIG. 7 is a graph of the uptake of tritiated (±)-FTC in human PBM cells (average of two determinations) in time (hours) versus pmol/$10^6$ cells.

FIG. 7 is a graph of the uptake of tritiated (±)-FTC in human PBM cells (average of two determinations) in time (hours) versus pmol/$10^6$ cells. The uptake studies indicate that radiolabeled FTC is readily taken up in human lymphocytes, that produce very large amounts of 5'-triphosphate.

EXAMPLE 9

Uptake of (±)-FTC into Human Liver Cells; HVB Activity of FTC

The same procedure was used with human liver cells as with PBM cells to determine uptake of FTC.

The (±)-FTC is taken up by hepG2 cells in large amounts. These human liver cells metabolize a large percentage of the (±)-FTC to (±)-FTC triphosphate.

These data in conjunction with other data indicate that (±)-FTC, as well as its (−) and (+) enantiomers, are effective as antiviral agents against HBV (hepatitis B virus).

EXAMPLE 10

Egress of (±)-FTC from Human PBM Cells

Studies were performed using radiolabeled FTC in order to follow the intracellular profiles of the parent drug and metabolites detected within the cell after removal of drug at different times after pulsing for 24 hours, the time needed for high levels of triphosphates to accumulate. Studies are conducted in duplicate. Uninfected cells (2–106 ml) are suspended in the appropriate medium supplemented with serum (10 ml per timepoint) and incubated at 37° C. in a 5% $CO_2$ incubator. Radiolabeled FTC concentration is 10 μM. After pulsing the cells with the labeled compound for the desired time, the cells are thoroughly washed and then replenished with fresh medium without the antiviral drugs (0 hr). At 0, 2, 4, 6, 12, 24, and 48 hours (second incubation time), the cells are removed, and immediately extracted with 60% cold methanol/water. The extract is obtained by centrifugation and removal of the cell pellet. The extracts are lyophilized and then stored at −70° C. Prior to analysis, the material is resuspended in 250 τl of HPLC buffer and immediately analyzed. Quantitation of intracellular parent drug and metabolic derivatives are conducted by HPLC, as follows.

Either a Micromeritics or Hewlett-Packard model 1090 PHLC system is used with an anion exchange Partisil 10 SAX column (Whatman, Inc.), at a flow rate of 1 ml/min, 1 kpsi pressure, using uv detection at 262 nm.

The mobile phase consists of:

a. deionized water
b. 2 mM $NaH_2PO_4$/16 mM NaOAc (pH 6.6)
c. 15 mM $NaH_2PO_4$/120.2 mM NaOAc (pH 6.6)
d. 100 mM $NaH_2PO_4$/800 mM NaOAc (pH 6.6)

Separation method: isocratic for 5 min with A, followed by a 15 min linear gradient to 100% B, followed by a 20 min linear gradient to 100% C, followed by 10 min linear gradient to 100% D, followed by 30 min isocratic with 100% D.

| | Retention times (minutes) in human cells: | | |
|---|---|---|---|
| Compound | Unchanged | Mono-phosphate | Diphosphate | Triphosphate |
| DLS-022 | 5.0 | 39.0 | 55.0 | 68.0 |
| BCH-189 | 3.5 | 40.0 | 55.0 | 69.0 |

Figure 8:
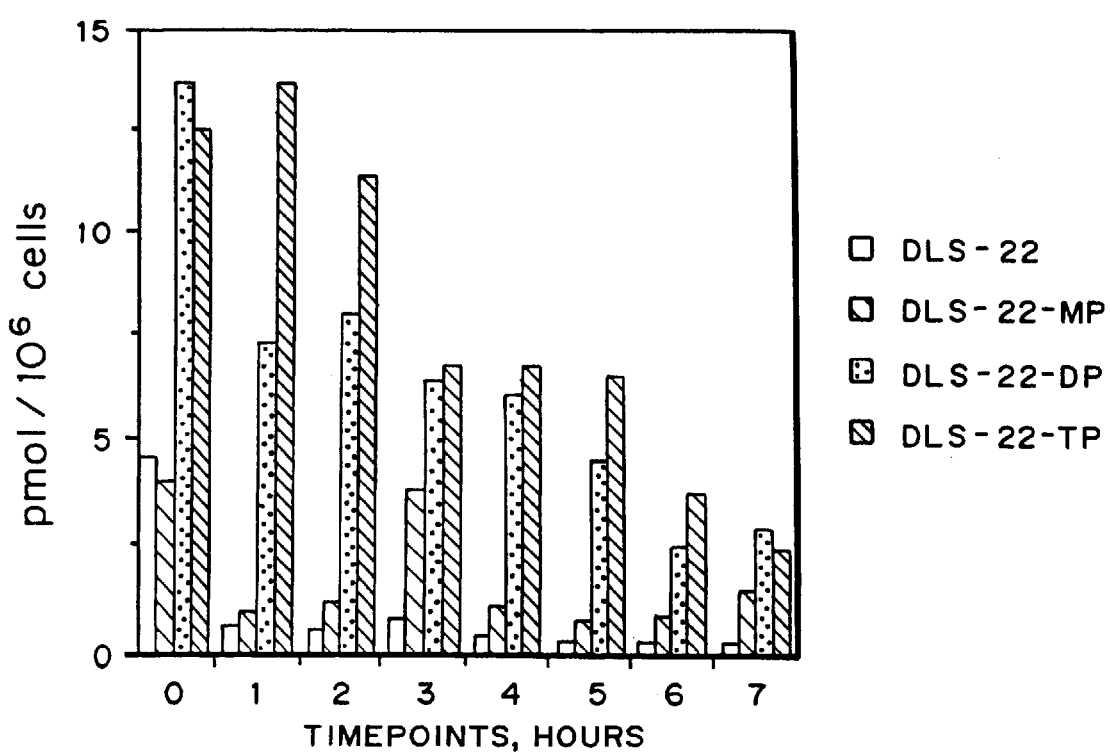
FIG. 8 is a graph of the egress of radiolabeled (±)-FTC from human PBM cells, measured in hours versus pmol/$10^6$ cells ((-darkened square-), (±)-FTC; (-///-), (±)-FTC monophosphate; (-// // //-), (±)-FTC diphosphate; and (-/// ///-), (±)-FTC triphosphate).

FIG. 8 is a graph of the egress of radiolabeled (±)-FTC from human PBM cells, measured in hours after drug removal versus concentration (pmol/$10^6$ cells). As indicated in the Figure, FTC-triphosphate has an intracellular half-life of approximately 12 hours and can be easily detected intracellularly at concentrations of 1–5 μM 48 hours after the removal of the extracellular drug, which is well above the $EC_{50}$ for the compound. Further, the affinity (K') for (±)-FTC triphosphate against HIV RT is 0.2 μM, below the 48 hour concentration level.

III. Preparation of Pharmaceutical Compositions

Humans suffering from diseases caused by HIV infection can be treated by administering to the patient an effective amount of (±)-FTC, or its (−) or (+) enantiomer or a pharmaceutically acceptable salt thereof in the presence of a pharmaceutically acceptable carrier or diluent. The active materials can be administered by any appropriate route, for example, orally, parenterally, intravenously, intradermally, subcutaneously, or topically, in liquid or solid form.

Pharmaceutically acceptable salts are known to those in the art and include those derived from pharmaceutically acceptable inorganic and organic acids and bases. Examples of suitable acids include hydrochloric, hydrobromic, sulfuric, nitric, perchloric, fumaric, maleic, phosphoric, glycollic, lactic, salicyclic, succinic, toluene-p-sulfonic, tartaric, acetic, citric, methanesulfonic, formic, benzoic, malonic, naphthalene-2-sulfonic and benzenesulfonic acids. Salts derived from appropriate bases include alkali metal (e.g., sodium), alkaline earth metal (e.g., magnesium), ammonium and quaternary amine.

The active compound is included in the pharmaceutically acceptable carrier or diluent in an amount sufficient to deliver to a patient a therapeutically effective amount of compound to inhibit viral replication in vivo, especially HIV and HBV replication, without causing serious toxic effects in the patient treated. By "HIV inhibitory amount" is meant an amount of active ingredient sufficient to exert an HIV inhibitory effect as measured by, for example, an assay such as the ones described herein.

A preferred dose of (−) or (±)-FTC will be in the range from about 1 to 20 mg/kg of bodyweight per day, more generally 0.1 to about 100 mg per kilogram body weight of the recipient per day.

The compound is conveniently administered in unit dosage form: for example containing 7 to 7000 mg, preferably 70 to 1400 mg of active ingredient per unit dosage form.

Ideally the active ingredient should be administered to achieve peak plasma concentrations of the active compound of from about 0.2 to 70 $\mu$M, preferably about 1.0 to 10 $\mu$M. This may be achieved, for example, by the intravenous injection of a 0.1 to 5% solution of the active ingredient, optionally in saline, or administered as a bolus of the active ingredient.

The concentration of active compound in the drug composition will depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

A preferred mode of administration of the active compound is oral. Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents. (±)-FTC, or its (−) or (+)-enantiomer or pharmaceutically acceptable salts thereof can be administered as a component of an elixir, suspension, syrup, wafer, chewing gum or the like. A syrup may contain, in addition to the active compounds, sucrose as a sweetening agent and certain preservatives, dyes and colorings and flavors. (±)-FTC, or its (−) or (+)-enantiomers, or pharmaceutically acceptable salts thereof can also be mixed with other active materials that do not impair the desired action, or with materials that supplement the desired action, such as antibiotics, antifungals, antiinflamnatories, or other antivirals, including other nucleoside anti-HIV compounds.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

The pharmaceutical composition can also include antifungal agents, chemotherapeutic agents, and other antiviral agents such as interferon, including $\alpha$, $\beta$, and gamma interferon.

If administered intravenously, preferred carriers are physiological saline or phosphate buffered saline (PBS).

In a preferred embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc.

Liposomal suspensions (including liposomes targeted to infected cells with monoclonal antibodies to viral antigens) are also preferred as pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, aractiadoyl phosphatidyl choline, and cholesterol) in an inorganic solvent that is then evaporated, leaving behind a thin film of dried lipid on the surface of the container. An aqueous solution of the active compound or its monophosphate, diphosphate, and/or triphosphate derivatives are then introduced into the container. The container is then swirled by hand to free lipid material from the sides of the container and to disperse. lipid aggregates, thereby forming the liposomal suspension.

IV. Preparation of Phosphate Derivatives of FTC

Mono, di, and triphosphate derivative of FTC can be prepared as described below.

The monophosphate can be prepared according to the procedure of Imai et al., *J. Org. Chem.*, 34(6), 1547–1550 (June 1969). For example, about 100 mg of FTC and about 280 $\mu$l of phosphoryl chloride are reacted with stirring in about 8 ml of dry ethyl acetate at about 0° C. for about four hours. The reaction is quenched with ice. The aqueous phase is purified on an activated charcoal column, eluting with 5% ammonium hydroxide in a 1:1 mixture of ethanol and water. Evaporation of the eluant gives ammonium FTC-5'-monophosphate.

The diphosphate can be prepared according to the procedure of Davisson et al., *J. Org. Chem.*, 52(9), 1794–1801 (1987). FTC diphosphate can be prepared from the corresponding tosylate, that can be prepared, for example, by reacting the nucleoside with tosyl chloride in pyridine at room temperature for about 24 hours, working up the product in the usual manner (e.g., by washing, drying, and crystallizing it).

The triphosphate can be prepared according to the procedure of Hoard et al., *J. Am. Chem. Soc.,* 87(8), 1785–1788 (1965). For FTC is activated (by making a imidazolide, according to methods known to those skilled in the art) and treating with tributyl ammonium pyrophosphate in DMF. The reaction gives primarily the triphosphate of the nucleoside, with some unreacted monophosphate and some diphosphate. Purification by anion exchange chromatography of a DEAE column is followed by isolation of the triphosphate, e.g., as the tetrasodium salt.

This invention has been described with reference to its preferred embodiments. Variations and modifications of the invention, a method of resolution and antiviral activity of nucleoside enantiomers, will be obvious to those skilled in the art from the foregoing detailed description of the invention. It is intended that all of these variations and modifications be included within the scope of the appended claims.

We claim:

1. The (−)-enantiomer of cis-4-amino-5-fluoro-1-(2-hydroxymethyl-1,3-oxathiolane-5-yl)-(1H)-pyrimidin-2-one that is at least 95% free of the corresponding (+)-enantiomer.

2. (−)-Cis-4-amino-5-fluoro-1-(2-hydroxymethyl-1,3-oxathiolane-5-yl)-(1H)-pyrimidin-2-one or a pharmaceutically acceptable salt, ester or salt of an ester thereof.

3. The substantially pure (−)-enantiomer of cis-4-amino-5-fluoro-1-(2-hydroxymethyl-1,3-oxathiolan-5-yl)-(1H)-pyrimidin-2-one or a pharmaceutically acceptable salt, ester, or salt of an ester thereof, wherein the (+) enantiomer is present in an amount of no more than 5% w/w.

4. The compound of claim 3 wherein the (+)-enantiomer is present in an amount of no more than about 2% w/w.

5. The compound of claim 3 wherein the (+)-enantiomer is present in an amount of less than 1% w/w.

6. A pharmaceutical composition comprising a compound as claimed in any one of claims 2–5 in combination with a pharmaceutically acceptable carrier.

7. (−)-Cis-4-amino-5-fluoro-1-(2-hydroxymethyl-1,3-oxathiolane-5-yl)-(1H)-pyrimidin-2-one or a pharmaceutically acceptable salt thereof.

8. The 5'-O-alkyl derivative of the (−)-enantiomer of cis-4-amino-5-fluoro-1-(2-hydroxymethyl-1,3-oxathiolane-5-yl)-(1H)-pyrimidin-2-one.

9. The 5'-O-alkylC(O)-derivative of the (−)-enantiomer of cis-4-amino-5-fluoro-1-(2-hydroxymethyl-1,3-oxathiolane-5-yl)-(1H)-pyrimidin-2-one.

10. The derivative of claim 9, wherein alkylC(O)— is selected from the group consisting of acetic, propionic, butyric, and pentanoic.

11. The monophosphate, diphosphate, or triphosphate of the (−)-enantiomer of cis-4-amino-5-fluoro-1-(2-hydroxymethyl-1,3-oxathiolane-5-yl)-(1H)-pyrimidin-2-one.

12. A pharmaceutically acceptable salt of the (−)-enantiomer of cis-4-amino-5-fluoro-1-(2-hydroxymethyl-1,3-oxathiolane-5-yl)-(1H)-pyrimidin-2-one that is at least 95% free of the corresponding (+)-enantiomer.

13. A pharmaceutical composition comprising an effective HIV treatment amount for humans of the (−)-enantiomer of cis-4-amino-5-fluoro-1-(2-hydroxymethyl-1,3-oxathiolane-5-yl)-(1H)-pyrimidin-2-one that is at least 95% free of the corresponding (+)-enantiomer, in combination with a pharmaceutically acceptable carrier or diluent.

14. A pharmaceutical composition comprising an effective HIV treatment amount for humans of the (−)-enantiomer of a pharmaceutically acceptable salt of a compound of cis-4-amino-5-fluoro-1-(2-hydroxymethyl-1,3-oxathiolane-5-yl)-(1H)-pyrimidin-2-one that is at least 95% free of the corresponding (+)-enantiomer, in combination with a pharmaceutically acceptable carrier or diluent.

15. The pharmaceutical composition of claim 13, in a form for oral administration.

16. The pharmaceutical composition of claim 15, wherein the composition is in tablet form.

17. The pharmaceutical composition of claim 15, wherein the composition is in capsule form.

18. The pharmaceutical composition of claim 13, wherein the composition is a liquid.

19. The pharmaceutical composition of claim 13, in a form for intravenous administration.

20. The pharmaceutical composition of claim 19, wherein the carrier comprises a sterile diluent for injection.

21. The pharmaceutical composition of claim 13, in a form for topical administration.

22. The pharmaceutical composition of claim 14, in a form for oral administration.

23. The pharmaceutical composition of claim 22, wherein the composition is in tablet form.

24. The pharmaceutical composition of claim 22, wherein the composition is in capsule form.

25. The pharmaceutical composition of claim 14, wherein the composition is a liquid.

26. The pharmaceutical composition of claim 14, in a form for intravenous administration.

27. The pharmaceutical composition of claim 17, wherein the carrier comprises a sterile diluent for injection.

28. The pharmaceutical composition of claim 14, in a form for topical administration.

* * * * *